United States Patent [19]
Hayashi et al.

[11] Patent Number: 5,262,839
[45] Date of Patent: Nov. 16, 1993

[54] METHOD AND APPARATUS FOR DETECTING STAINLESS STEEL SENSITIZATION

[75] Inventors: Makoto Hayashi; Hideyo Saito; Tadakazu Oguri, all of Hitachi, Japan

[73] Assignee: Hitachi, Ltd., Tokyo, Japan

[21] Appl. No.: 852,549

[22] Filed: Mar. 17, 1992

[30] Foreign Application Priority Data

Mar. 19, 1991 [JP] Japan .................................. 3-054646

[51] Int. Cl.⁵ ...................... G01N 21/88; G01N 23/20
[52] U.S. Cl. ...................................... 356/36; 356/237; 356/384
[58] Field of Search .................. 356/36, 237, 239, 384, 356/387

[56] References Cited

U.S. PATENT DOCUMENTS 4,548,903 10/1985 Weiss et al. ...................... 356/36 X
4,725,884 2/1988 Gurnell et al. .................. 356/384 X

FOREIGN PATENT DOCUMENTS 62-119445 5/1987 Japan .

Primary Examiner—Vincent P. McGraw
Attorney, Agent, or Firm—Antonelli, Terry, Stout & Kraus

[57] ABSTRACT

The susceptibility of austenitic stainless steel is tested by inputting a highly magnified image of the polished and etched steel surface through a microscope, a CCD camera and an input device into an image processor. The image processor is set up to identify grain boundary locations in the image, take width measurements across the grain boundaries, based on luminance distribution, and calculate average and maximum values for the measured widths. These calculated measured values are compared with experimentally-determined reference values − 1 to 1.5 μm for mean width and 2 to 3 μm for maximum width - and a susceptibility status determined accordingly. The status can then be output using a display e.g. screen or printer.

26 Claims, 13 Drawing Sheets

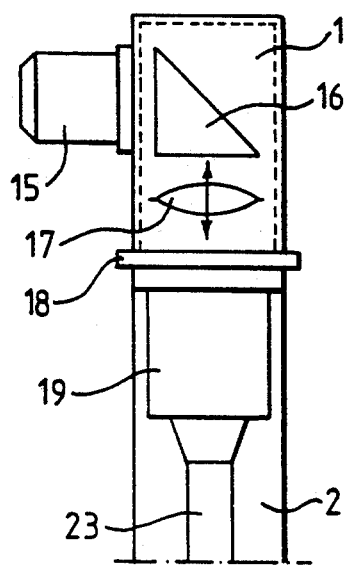
Fig. 12.
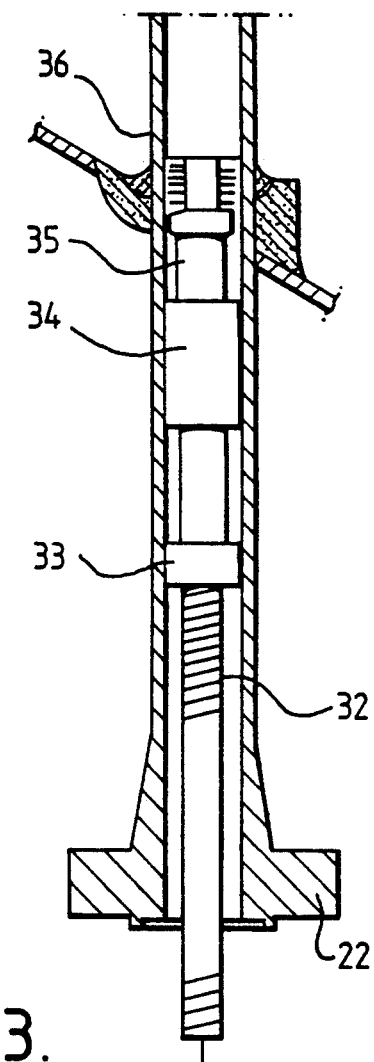
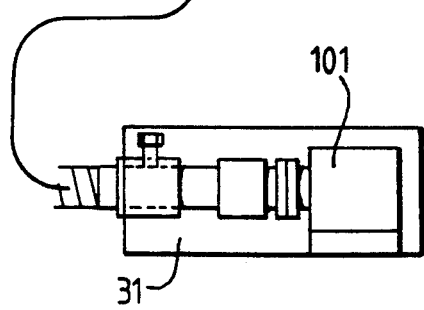
Fig. 13.

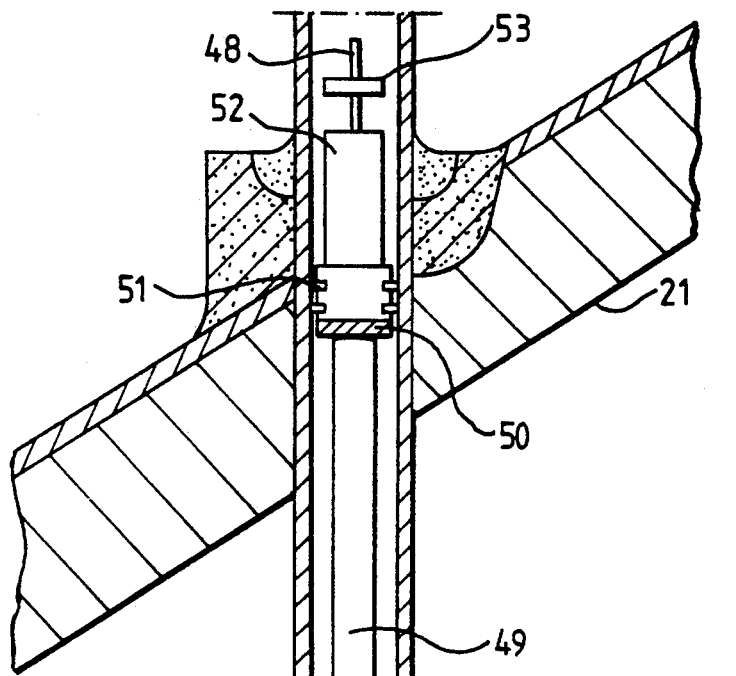
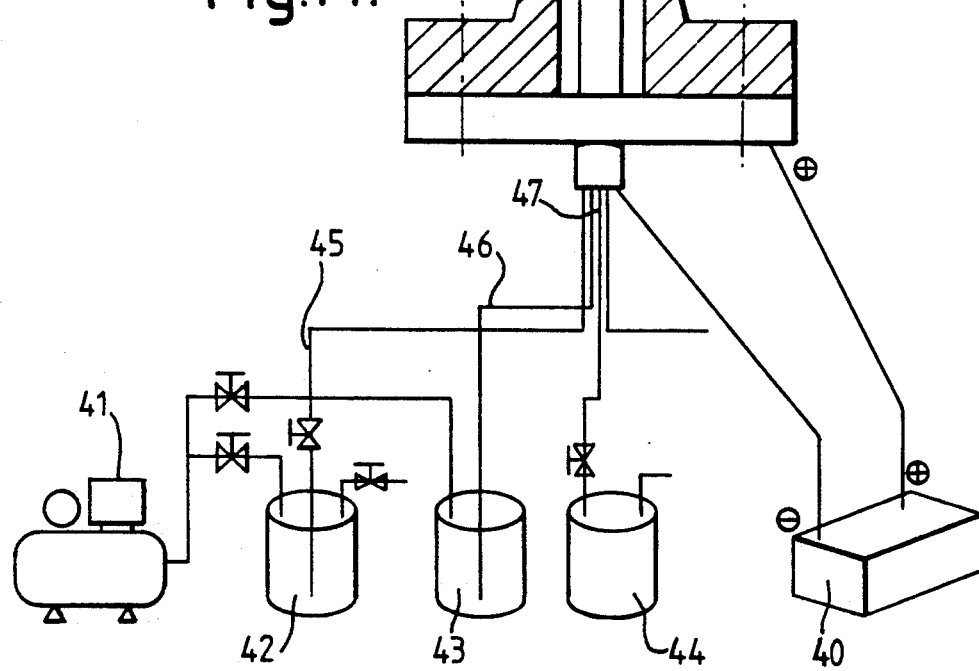
Fig.14.

METHOD AND APPARATUS FOR DETECTING STAINLESS STEEL SENSITIZATION

FIELD OF THE INVENTION

This invention relates to methods and apparatus for testing austenitic stainless steel, in particular to assess the susceptibility thereof to stress corrosion cracking (SCC).

BACKGROUND OF THE INVENTION

SCC is a problem with austenitic stainless steel in conditions where the steel is subjected to heat. As supplied, the steel has a generally homogeneous distribution of chromium (Cr). Conventionally this is by a solution heat treatment at from 1000°–1150° C., which causes uniform dispersion of Cr in the material. However, it is known that periods of heating at intermediate temperatures, in particular 550°–850° C., result in the precipitation of carbide (e.g. $M_{23}C_6$ where M is primarily Cr, but also Fe and to some extent Ni) at grain boundaries of the steel. This reduces corrosion resistance, a phenomenon called sensitization. In practice it may be caused by welding heat. For experiment it can be created by heating the steel at 750° C. for 30 minutes, and then at 500° C. or 620° C. for 24 hours. As the treatment progresses, carbide initially precipitates at grain boundaries as a number of independent bodies which then grow, combine with one another and cover the grain boundary. As the heat treatment continues further, the carbide spreads on the boundaries, to a width depending to some extent on the nature of the respective grain boundary. For example, where crystals are twins i.e. have symmetrical inclined grain boundaries, very little carbide separates at the boundary even after long heat treatment.

Adjacent the boundary, the austenite has regions where chromium is depleted. See FIG. 1 which is a typical representation of chromium concentration across a grain boundary. The substantial presence of carbide $M_{23}C_6$ at the grain boundary 100 (width W) is seen, also regions of austenite $L_{-CR}$ adjacent the boundary, depleted in chromium relative to the prevailing 18 wt %. It has been found that, where the chromium concentration falls below a level CRL of about 13%, the steel is "sensitized": corrosion resistance decreases and susceptibility to SCC increases. The width W' of the region below the corrosion resistance limit CRL may be some tens of nm wide in sensitized steel.

It is important to know if steel has become susceptible to SCC, particularly in structures such as nuclear power plants and chemical reactors, which must keep their integrity.

DESCRIPTION OF PRIOR ART

Accordingly, various methods have been developed in the prior art for testing steel for its susceptibility to SCC.

One widely used method is electrochemical potentiokinetic reactivation, in which a contained KSCN electrolyte is placed against the steel surface, between electrodes, and current monitored while voltage is slowly scanned up and down. If the steel is sensitized, the voltage sweep corrodes the grain boundaries and a characteristic current path, depending on the area corroded, is observed. The technique is used for standardization of steel, also for commercial testers.

It has the disadvantage that it can only be used in situ at exposed locations where there is sufficient space, since the apparatus is rather bulky. It is also very slow; the steel must first be polished (about 10 minutes) and the EPR process takes about 1 hour.

Another technique is the Strauss test, in which the steel surface is treated with copper sulphate and the depth of the resulting cracks is measured. A depth greater than about 50 μm indicates sensitization. However this technique is not of any use at installations in situ because the steel must be cut to measure the crack depth.

Because of the problems of the above techniques in actual situations, it is in fact normal practice for SCC susceptibility to be monitored by trained examiners. A portion of the steel surface is polished and etched, typically with oxalic acid, and then examined visually by the examiner under magnification of 100 to 200X. As the result of long training, the examiner learns to distinguish between the appearance of sensitized and nonsensitized steels. It is however impossible for inexperienced examiners to carry out the task reliably. When a large amount of steel needs to be checked, experienced examiners (who are few) must work manually on individual portions of the metal surface. Inevitably this procedure is very time-consuming.

SUMMARY OF THE INVENTION

The problem addressed herein is to provide novel means and methods for testing austenitic stainless steel for this sensitization. Most preferably, it is sought to provide means and methods which can enable a reliable examination of the steel to be carried out by ordinary personnel, without the need to cultivate special examination skills, and in a relatively short time.

The present inventors have made careful studies to determine what properties of a heat-affected steel surface can be determined conveniently by apparatus, without requiring a high degree of experience or skill of an operator, but nevertheless providing a reliable indication of whether the surface is sensitized or not, or an indication of the degree of sensitization.

In one aspect, we propose a method for testing austenitic stainless steel in which the steel is first polished and etched e.g. by conventional etching with oxalic acid, followed by inputting an image of the polished and etched surface, through an optical microscope, into an image processor;

using the image processor to measure a boundary width at an etched grain boundary, using the distribution of brightness across the grain boundary in the input image, and comparing the measured boundary width with a predetermined reference width.

In another aspect, the invention provides apparatus for testing austenitic stainless steel to assess its susceptibility to stress corrosion cracking, comprising:

an image processor having means for receiving a magnified image of the polished and etched steel surface, from an optical microscope; and means for measuring the boundary width in the image at a grain boundary, using the distribution of brightness in the image.

Means may furthermore be provided for displaying the result of the comparison as a susceptibility value (e.g. a number on a scale) or as a status (e.g. susceptible/not susceptible).

The present invention has been made possible by researches made by the inventors, in which they have been able to discover a new relationship to correlate the susceptibility of steel with specific width data relating to the observed grain boundary phenomena.

In particular, the technique may measure plural boundary widths, calculate a mean width from these measurements, and compare the mean width with a reference mean width. Usually, such a reference mean width will be fixed in the range from 1–1.5 μm.

Alternatively, or preferably additionally, the technique notes the maximum width among plural measured widths, and compares it with a predetermined reference maximum width. The reference maximum width is generally in the range from 2–3 μm.

In apparatus, these functions may be fulfilled by purpose-built comparators and stores, or by appropriate programming of a dedicated control processor e.g. microprocessor.

In a further aspect, the invention provides apparatus for use in determining the susceptibility of austenitic stainless steel to stress corrosion cracking, comprising
an optical microscope;
drive means for adjusting the position of the optical microscope in relation to a sample to be tested;
an image processor for receiving a magnified image of the sample from the optical microscope;
means for selecting a measurement sub-area from the received image, and taking a plurality of boundary width measurements in said measurement sub-area at grain boundary locations of the image;
means for determining a mean width from the plural width measurements;
means for comparing the mean width with a predetermined reference mean width, and
means for displaying a susceptibility status for the sample, in dependence on said comparison.

In a still further aspect, we provide a method for testing austenitic stainless steel in relation to its corrosion resistance, comprising polishing and etching the surface of the steel, measuring the width at a plurality of grain boundaries of the steel of a dark, chromium depleted zone, calculating a mean of the measured zone widths, comparing the mean with a reference value fixed between 1 and 1.5 μm, and outputting the result of the comparison.

In a still further aspect, the invention provides means and a method for use in testing a steel surface at a confined location. An elongate member is provided which can extend to the desired location, and which has at least one seal which seals against the steel surface to define a fluid space. Fluid for electrolytic etching e.g. oxalic acid, is fed along the elongate member to the fluid location from an etching fluid supply. The apparatus has an electrode provided in the fluid space, which is remotely activated to effect electrolytic etching. The etching fluid is then drained, and a rinsing fluid e.g. an alcohol is sent to the fluid location from a rinsing fluid supply to rinse the etched surface.

The fluids may be driven by compressed air. Initiation of the process steps may be substantially automatic e.g. microprocessor controlled.

DETAILED CONCEPT DESCRIPTION

We now give a more detailed description of the concepts underlying the invention.

FIGS. 2 and 3 are typical representations of magnified steel surfaces after polishing and electrolytic etching with oxalic acid. The steel is type 304 austenitic stainless steel. The surface of FIG. 2 shows grain boundaries after a heat treatment for uniform solution of Cr. The grain boundaries (black lines) are quite narrow. FIG. 3 shows a sample after a heat treatment sensitizing it to corrosion. The black lines are much wider.

The present inventors appreciated that the width of these lines has some correlation with the degree of sensitization i.e. the degree of reduction in corrosion resistance. It is true that the perceived boundary width after etching shows only the width of chromium-lacking layers. It does not show the distribution of chromium concentration nor the depth of the layers. But, the width of the layers does reflect the sensitization condition to some extent.

The inventors have therefore made investigation of this correlation. They measured a large number of grain boundary widths after etching. More accurately, they measured the width of chromium depleted layers at etched grain boundaries. The actual grain boundaries themselves remain narrow. The material used was type 304 austenitic stainless steel which contains 0.06% of carbon; sufficient for sensitization to occur. The steel was kept at 1150° C. for 30 minutes and cooled with water, so that chromium was homogeneously dispersed.

The steel was then heat treated at 620° C. for sensitization. Sample surfaces which had been treated respectively for 0,15,60,120,180,300,600 and 1440 minutes at 620° C. were respectively polished to a mirror-like finish, etched electrolytically with 10% oxalic acid, and about 5 photographs were taken from different portions of the prepared surface magnified to 400 x actual size by a microscope. The photographs were of the type shown in FIGS. 2 and 3. The widths of all of the apparent grain boundaries (really, the chromium-depleted layers) in the photographs were measured by a person. The boundaries were measured at portions substantially straight for at least a few μ m, to avoid distortion of the data by bends. About 70 measurements were taken, maximum and mean widths calculated, and the data assembled.

FIG. 4 shows how the mean boundary width $W_{mean}$ and the maximum boundary width $W_{max}$ changed as heat treatment progressed. Little change was observed up to 15 minutes of treatment. After 60 minutes, the widths increased rapidly, $W_{max}$ and $W_{mean}$ reaching a steady level or saturation at about 180 minutes.

From previous studies of these steels, it is known that susceptibility to SCC begins at about 60 minutes of 620° C. treatment, sometimes up to 90 minutes. By comparison with the data, the inventors therefore deduced that this could be correlated with $W_{max}$ equals about 2 μm and $W_{mean}$ equals about 1 μm, or slightly more.

On the basis of the above, the following embodiments were developed and these are now described with reference to the accompanying drawings.

BRIEF DESCRIPTION OF THE DRAWINGS

FIG. 12 shows a measuring head thereof, enlarged;

FIG. 13 shows apparatus, embodying the invention, for polishing the steel surface;

FIG. 14 shows apparatus, embodying the invention, for etching the polished surface.

FIG. 16 shows a selected measurement area on a monitor screen, while

FIGS. 1 to 4 have already been described.

DETAILED DESCRIPTION OF THE PREFERRED EMBODIMENTS

Figure 1:
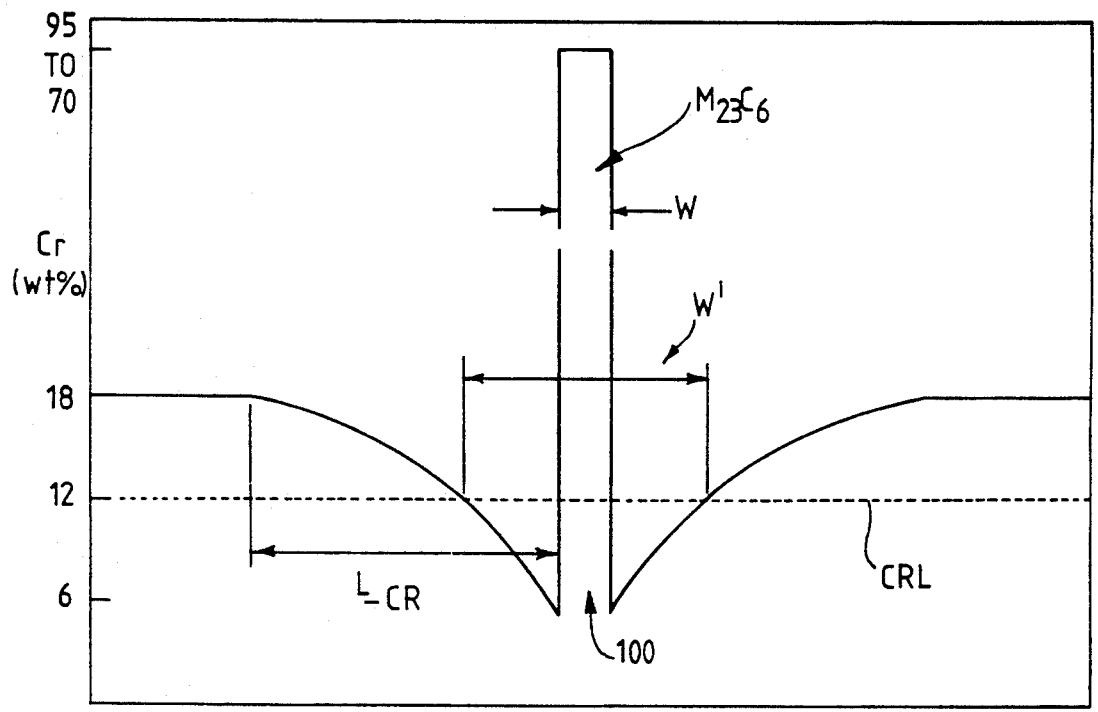
FIG. 1 (already described) shows the distribution of chromium across a grain boundary.
Figure 2:
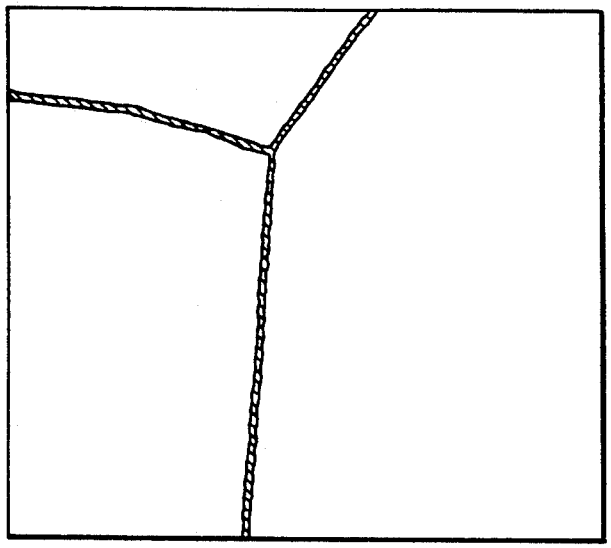
FIGS. 2 and 3 are magnified photographs showing polished and etched grain boundaries before and after sensitizing heat treatment.
Figure 3:
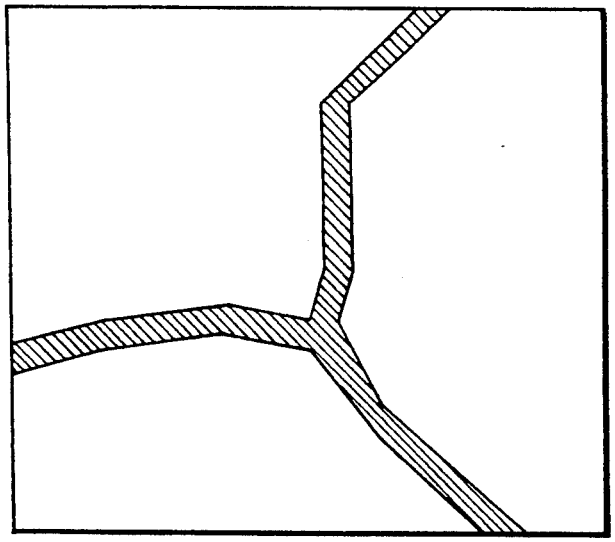
Figure 4:
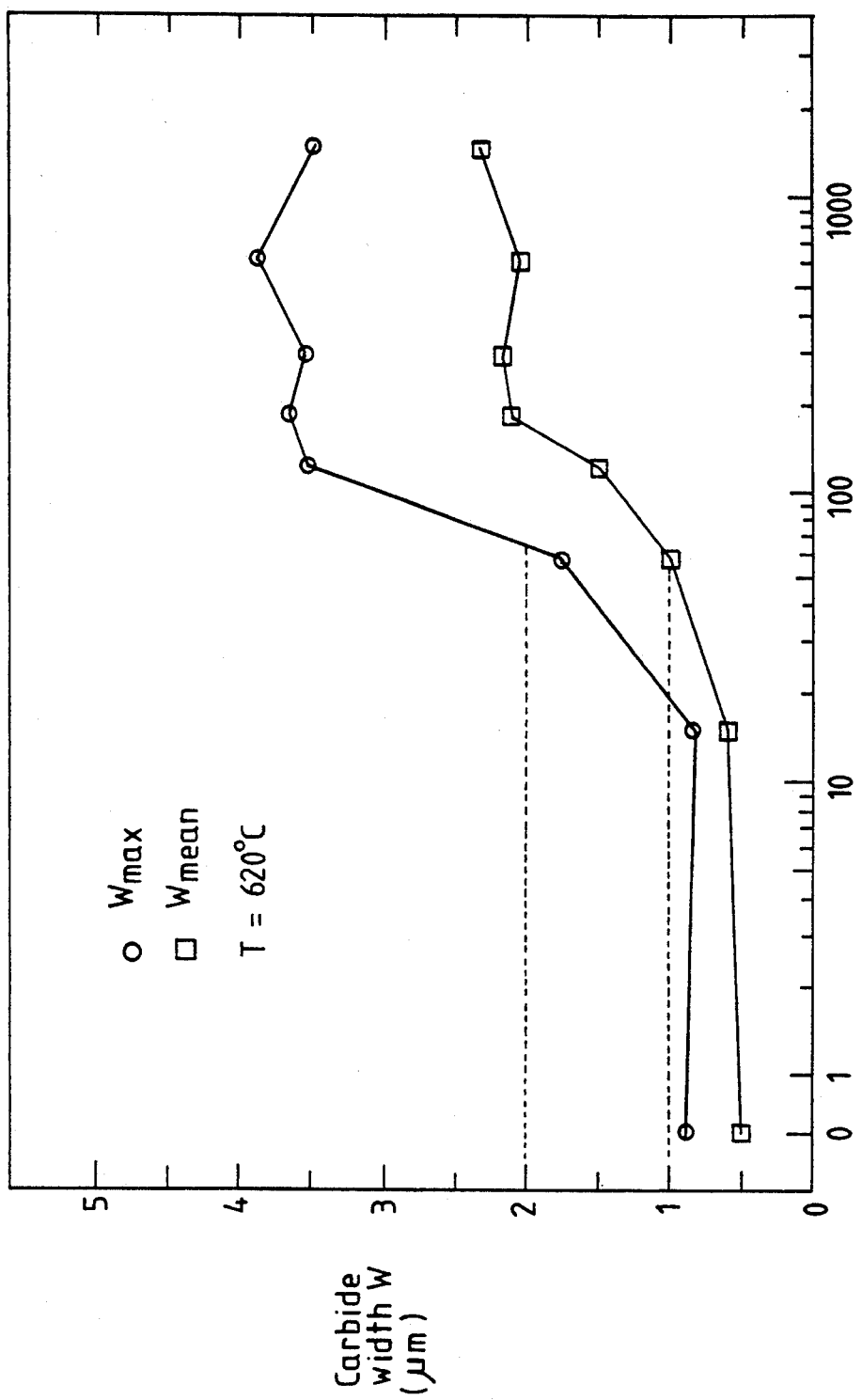
FIG. 4 shows variation of maximum and mean measured boundary widths according to time of sensitizing heat treatment.
Figure 5:
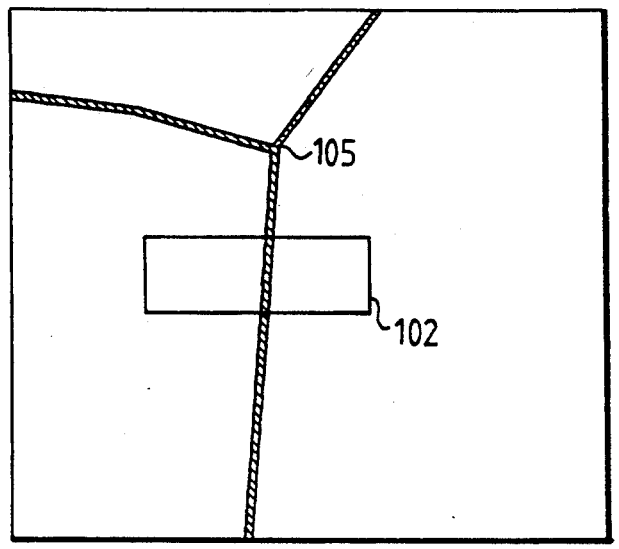
FIGS. 5 and 6 represent monitor screen displays of non-sensitized and sensitized sample images.
Figure 6:
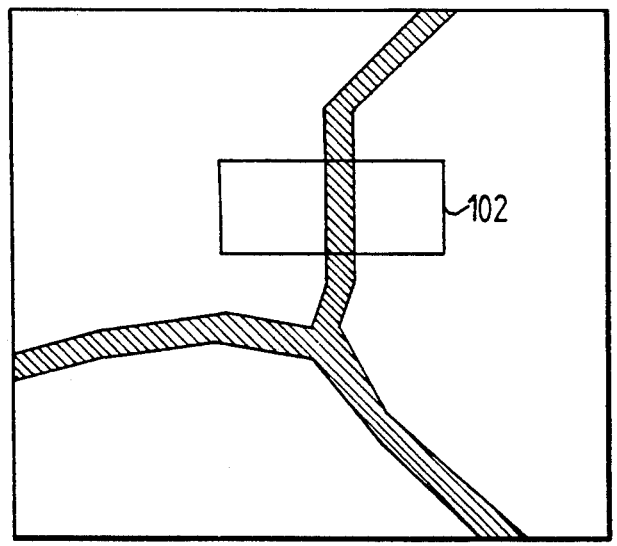

FIGS. 5 and 6 show how magnified metal structure images will look, as obtained with a microscope, pictured using a CCD (charge coupled device) camera, and input to an image processor, with a monitor screen, to measure the distribution of luminance or brightness. FIG. 5 shows non-sensitised steel after etching; FIG. 6 shows steel after treatment at 620° C. for 600 minutes. The FIG. 5 sample shows a grain boundary line extending substantially vertically up the middle of the screen, with a width of about 0.8 μm. Other boundary lines are seen, meeting at a triple-point or junction 105. The FIG. 6 image includes a grain boundary extending substantially vertically, with a perceived width of about 2.5 μm.

The procedure requires a substantial magnification of the image, much larger than the mild magnification used by an examiner. The microscope used magnifies the surface 200–400 times. The image processor in this embodiment is capable of achieving 4 or 5 x magnification. Generally, overall magnification of at least 200 x is desired before measurements are taken.

FIGS. 5 and 6 also show a rectangular measurement area 102 over which the image processor is programmed to scan a horizontal distribution of luminance. The position of the window defining the measurement area 102 can be moved around the screen by an operator e.g. using a mouse.

Figure 7:
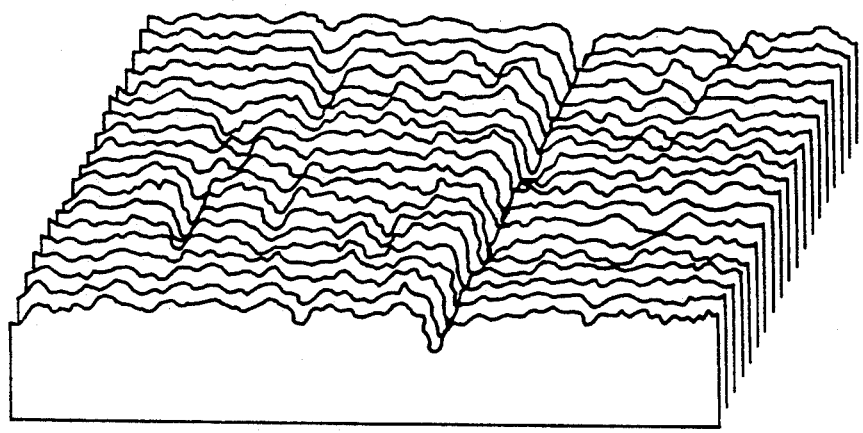
FIGS. 7 and 8 show luminance measurement results for the measurement areas of FIGS. 5 and 6 respectively.
Figure 8:
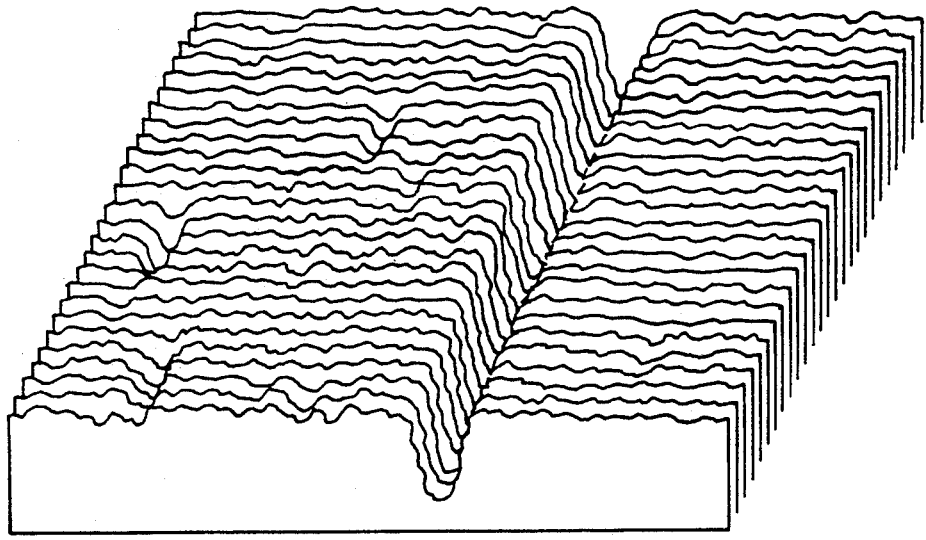

FIGS. 7 and 8 show, for each of FIGS. 5 and 6 respectively, the results of a series of luminance scans across the measurement area 102, made by the image processor. Polishing scratches and corrosion pits, which look black in microscope images, do have a low luminance. However they are only partial and local. The grain boundaries are identifiable by a low luminance region extending in a defined direction. The width of the "trenches" in the luminance distributions of FIGS. 7 and 8 were 0.96 and 2.8 μm respectively: slightly larger than those determined visually using the microscope image, but generally corresponding.

Figure 9:
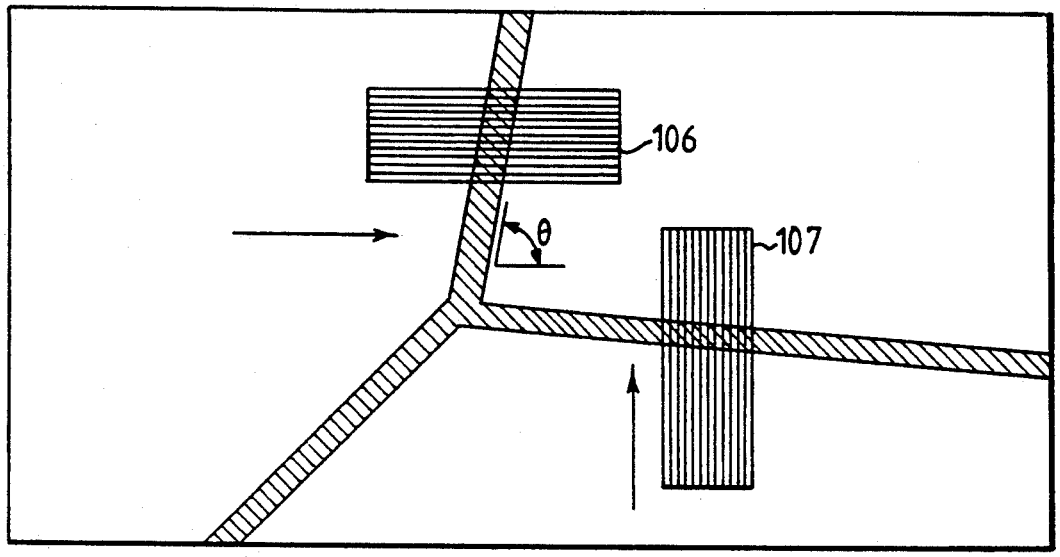
FIG. 9 illustrates selection of scanning directions according to grain boundary direction.
Figure 10:
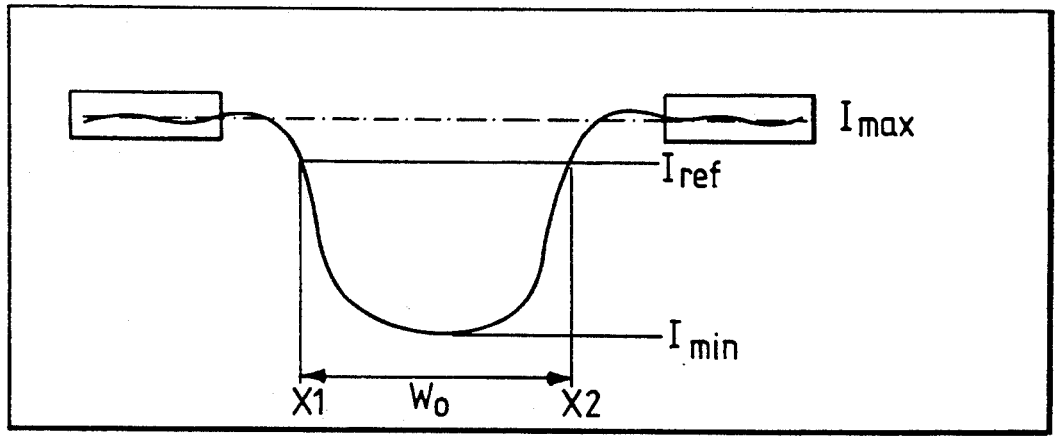
FIG. 10 shows the basis of one way of determining the limits of a measured boundary.

FIG. 9 shows how two scanning directions can increase the measurements available. Generally speaking, the directions of grain boundaries are not orderly. If distribution can only be scanned in a horizontal direction, boundaries extending near to horizontal cannot be measured with any precision. Therefore, when a grain boundary is closer to horizontal, the luminance distribution is scanned vertically instead. The Figure shows a measurement area 106 in which a number of scans have been made horizontally across a nearly-vertical boundary, and a second measurement area 107 in which vertical scans measure a nearly-horizontal boundary. A series of plural scans is made within the area, and these measurements are used to obtain a mean boundary width. There is some flexibility about the method adopted for nominating the edge of a boundary. Clearly some criterion is necessary to obtain consistent width values. The general characteristics of luminance distribution curves are seen from FIGS. 7, 8 and 10. The edge of the distribution dip at each boundary is not very sharply defined. The maximum luminance or brightness is that of the grains themselves. Even the value of this maximum luminance may however vary with irregularities of the steel surface, since the magnification is large.

In one approach, for each image, a number of maximum luminance values are taken, and a mean derived to give $I_{max}$. Then, luminances on grain boundaries are measured and a corresponding minimum luminance $I_{min}$ obtained. A threshold or reference luminance I can then be selected as an appropriate proportion of the difference between these, subtracted from $I_{max}$. That is:

$$I = I_{max} - \frac{(I_{max} - I_{min})}{X} \qquad (1)$$

If $X=2$, then I is a so-called full width at half maximum. Preferably X is greater than 2 e.g. 5, to correspond more closely with the perceived "edges" of the drop in luminance.

The co-ordinates (X1 and X2) of the intersections of the scanning line with this threshold luminance value I are obtained. See FIG. 10, where I is marked "$I_{ref}$" for clarity. The measurement is applied to all of n scanning lines in the measurement area. A provisional width value $W_o$ is obtained as follows:

$$W_o = \sum_i (|X2i - X1i|)/n \qquad (2)$$

The co-ordinates of the centre of the boundary are obtained as follows:

$$X_o = \frac{X2i - X1i}{2} \qquad (3)$$

From the set of grain boundary centre co-ordinates, an average angle $\theta$ between the boundary and the scanning direction of luminance measurement is determined, using a "least squares" method. An angle correction is then applied as follows, to obtain a true boundary width from the provisional boundary width:

$$W_d = W_o \sin \theta \qquad (4)$$

Other methods of selecting a threshold luminance are possible. One method is to specify the threshold luminance as a simple proportion of the value of the maximum luminance $I_{max}$, that is $$I = AI_{max} \quad (A \text{ is } <1) \tag{5}$$

For example, $A=0.95$.

Figure 11:
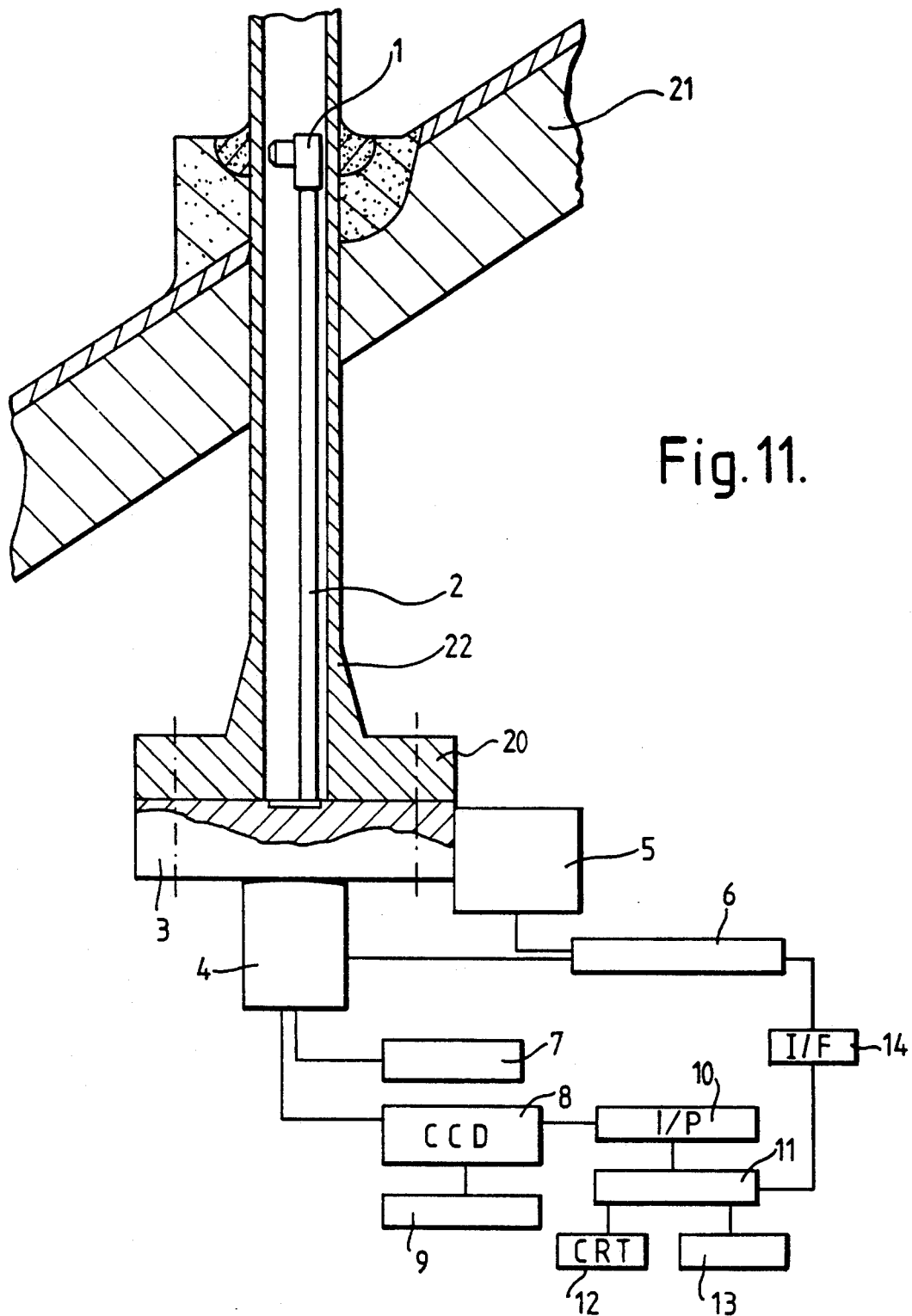
FIG. 11 shows, schematically, apparatus embodying the invention for inspecting the steel of an in-core monitor housing.

FIG. 11 is a diagram, largely schematic, of apparatus embodying the invention. The apparatus is adapted for checking sensitization status of steel in the in-core monitor housing 22 extending through, and welded into, the wall 21 of the pressure vessel of a boiling water reactor. An elongate probe stem 2 carries a measuring head 1 which can extend up inside the housing 22. The stem 2 is mounted on driving gear 3 which is positioned against a flange 20 at the outer end of the housing 22. The stem 2 is telescopic. The drive system 3 includes an elevating drive 4 for extending the telescopic stem 2 longitudinally, and a rotary drive 5 for rotating the stem 2 and head 1. The two drives 4,5 are connected to a computer control 11 by way of a scanner driving unit 6 and an interface 14, so that driving can be controlled either fully automatically or, more usually, by input to the computer keyboard.

FIG. 12 shows in more detail how the inspection head 1 comprises components of a microscope. Light from the sample surface enters an objective lens 15 of long focal length, is bent 90° by a half-rectangular prism 16 and passes through a focusing lens 17 and an ocular 18. A small charge coupled device camera 19 forms the image from the incoming light, and the image is sent down the stem 2 via an optical fibre 23 to a CCD camera input section 8 (see FIG. 11). The image signal from the camera input section 8 is monitored by a monitor 9 and sent to an image processor 10. Such equipment is known in itself, and a skilled person will not have difficulty adapting it to the present use. The image processor 10 is controlled by the control computer 11 to make the various scans mentioned above and to calculate the luminance distribution and boundary width on one of the suggested bases. The measured luminance distributions and calculated widths may be displayed on the screen of a cathode ray tube 12 and/or printed by a printer 13.

A general test procedure can be described by the following ordered steps.

(A) The sample surface is polished e.g. with emery paper or a flapper wheel. See later.
(B) The polished surface is etched electrolytically e.g. with oxalic acid, to reveal the metal structure. See later.
(C) The microscope of the inspection head 1 is inserted and moved adjacent the portion of structure to be observed; an image formed by the microscope is input through the CCD camera 19.
(D) Distributions of luminances across grain boundaries are measured.
(E) The luminance distribution is used to derive boundary width values.
(F) Boundary width reference criteria are used, using comparisons, to assess the measured boundary widths to decide the degree of sensitization.
(G) The surface is again polished, either electrolytically or e.g. with a flapper wheel, to remove minute notches caused in the surface by the etching.

FIG. 13 shows apparatus suitable for the polishing procedure. Motor-powered driving gear 31 is installed adjacent the opening of the ICM housing 22, to drive a flexible shaft 32 is insertable into the housing 32, supported by guide rings 33,34. A chuck 35 is on the end of the shaft 32, and can hold a suitable polishing member e.g. a flapper wheel 36, so that the motor 101 can be used to drive the polishing action when the polishing member reaches the desired location.

FIG. 14 is a diagram, largely schematic, showing apparatus for a subsequent etching step. Apparatus positioned outside the ICM housing 22 comprises electrolytic corrosion apparatus 40, a compressed air source 41, an etching fluid source 42, e.g. a tank for 10% oxalic acid, a rinsing fluid source 43 e.g. a tank of alcohol, a return tank 44, an etching fluid supply pipe 45, a rinsing fluid supply pipe 46 and a return pipe 47. The head of the apparatus comprises an elongate probe 49 for insertion into the housing 22. A soft O-ring type seal 51 surrounds the probe near its end, to seal against the inside wall of the housing 22. Above the seal 51, the probe has a cylindrical electrode 52 (connected back to the negative electrode of the corrosion apparatus 40), an air vent pipe 48 and openings of the oxalic acid and alcohol supply pipes 45,46. An insulator 50 is provided below the seal 51, to insulate the probe 49 from the electrode 52. The positive electrode of the corrosion apparatus 40 is connected to the ICM housing 22.

The etching procedure follows the following steps.
(A) The probe 49 is inserted into the housing 22.
(B) The cylindrical electrode 52 is positioned at the desired measurement location.
(C) By opening the appropriate inlet valve, compressed air from source 41 is sent to the oxalic acid tank 42, driving oxalic acid through the supply pipe 45 to the location above the seal 51. The oxalic acid fills the region of the housing above the seal, around the electrode 52. Compensation air escapes through vent pipe 48.
(D) The oxalic acid tank outlet is closed.
(E) At the same time, the return inlet valve for oxalic acid is closed, so that the acid is kept at the region around the electrode 52.
(F) Electrolytic corrosion apparatus 40 is switched on, to cause electrolytic etching for a predetermined period.
(G) When etching is completed, the oxalic acid tank outlet valve is opened.
(H) At the same time an air vent for the upper part of the oxalic acid 42 is opened, to return the oxalic acid from around the electrode 52 to the oxalic acid tank.
(I) Compressed air is sent from the source 41 to the alcohol tank 43, driving alcohol through the supply pipe 45 to alcohol spray nozzle 53, rinsing and cleaning the etched location.
(J) At the same time, the return pipe 47 is opened so that the residual electrolytic solution and the cleaning alcohol can return to the return tank 44.
(K) The housing is preferably cleaned as the examination apparatus is being removed.

When the microscope apparatus (FIG. 11) is inserted, there may not initially be a grain boundary suitable for measurement within the measurement range which is displayed initially at the centre of the monitor screen 9. The apparatus therefore has the capability to change the measurement scanning direction in response to a perceived boundary direction, changing the measurement position relative to the image on the screen, changing the observation position by initiating movement of the measuring apparatus, and changing the size of the measurement area.

Figure 15:
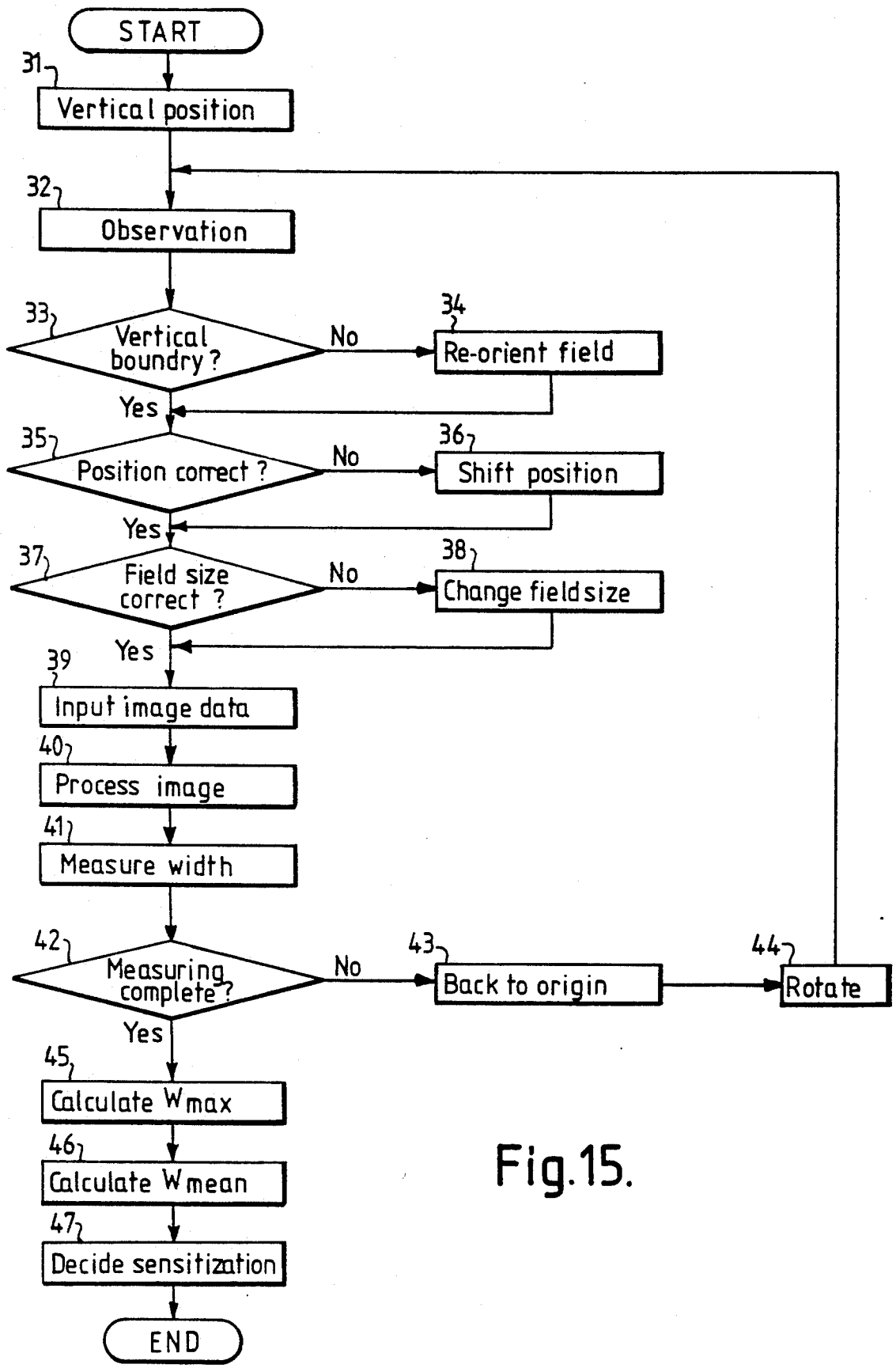
FIG. 15 is a flow chart for a process of determining sensitization status.

FIG. 15 sets out the process steps for an embodiment of control apparatus having this capability. The steps are explained below.

(31) Position the measuring head 1 vertically.

(32) Make a preliminary examination of metal structure. The apparatus is initialised to make a luminance distribution measurement of a grain boundary stretching vertically relative to the screen.

Figure 16:
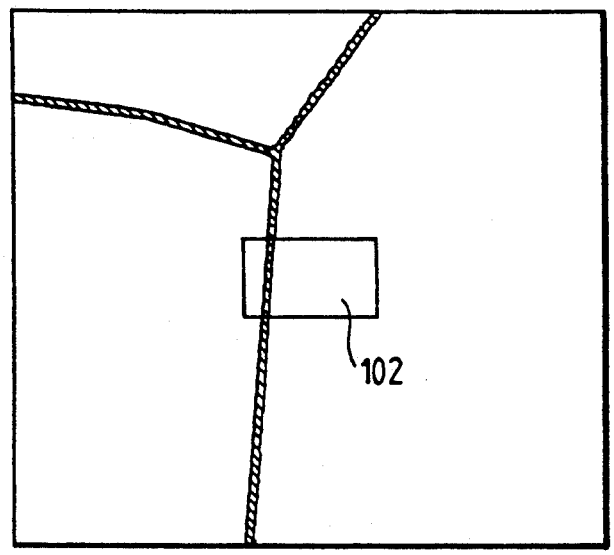

(33) Check if the grain boundary to be examined is a vertically-extending one. For example, if as shown in FIG. 16 a vertical boundary is in the measurement area at the centre of the monitoring screen 9, the operation can continue.

Figure 17:
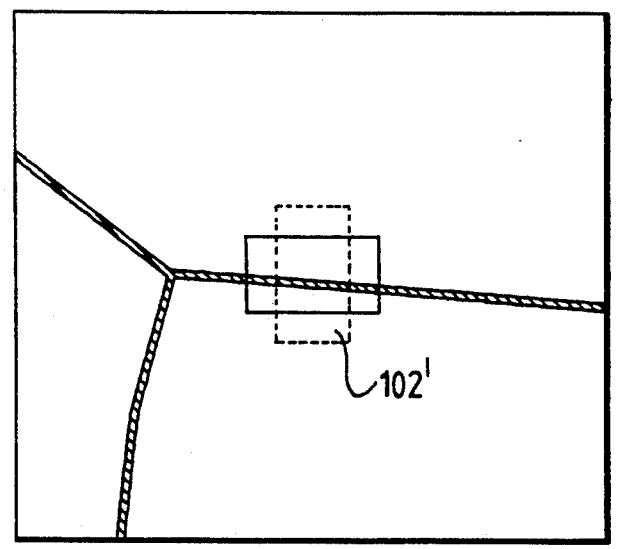
FIGS. 17, 18 and 19 show possibilities for turning, shifting, enlarging and reducing the measurement area, and FIG. 20 schematically shows apparatus, embodying the invention, for determining susceptibility status by inspecting a replica.

(34) If however the boundary in the measurement area is generally horizontal (FIG. 17) the orientation of the visualised measurement field is changed by 90°, as shown by the dotted and solid rectangles in FIG. 17.

(35) The observation position is checked. A grain boundary in the measurement area should be generally straight to produce a reliable reading.

Figure 18:
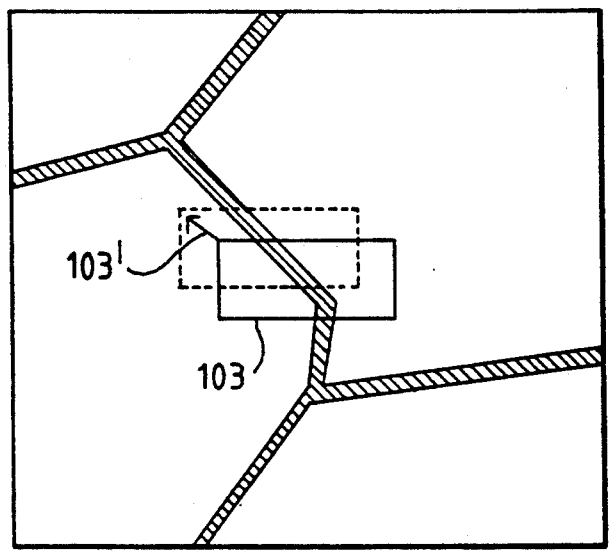

(36) If for example the boundary in the measurement area is found to be bent (FIG. 18) the computer 11 controls the image processor 10 to move the measurement area 103 to a location such as 103' covering a straight boundary portion. Alternatively it is possible for the computer 11 to adjust, via the scanner driving unit 6, the drivers 4,5 to move the measuring head 1 to a different position so that the measurement area on the monitor 9 crosses a straight or a relatively straight boundary.

Figure 19:
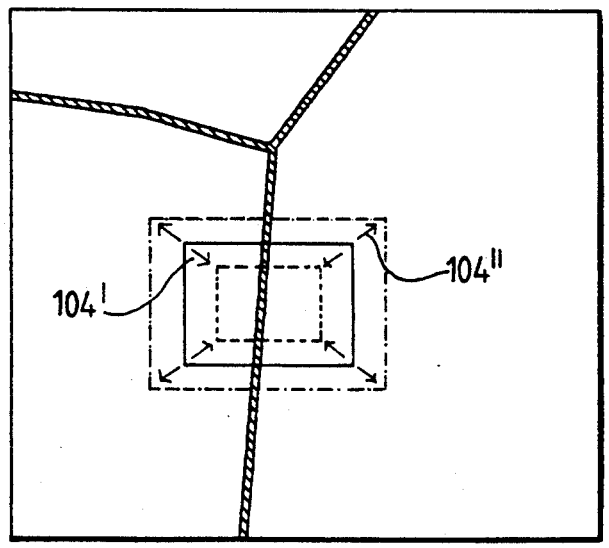

(37) Measurement and field size is checked. If steps (33) to (36) above have produced a suitable boundary, the measurement can continue but, if a boundary is blurred e.g. because of poor etching, or if for other reasons a more precise value is likely to be obtained by enlarging the field, then the size of the measurement area i.e. visual field size is adjusted (see adjusted sizes 104', 104" in FIG. 19).

(38) When specification of the measurement area is satisfactory, the image data is input to the image processor 10.

(39) The image processor processes the image to measure the distribution of luminances across the grain boundary.

(40) The distribution of luminances is processed to calculate the width of the boundary.

(41) A check is made, to see if all measurements have been completed with the detection apparatus in the specified vertical position.

(42) If not all measurements have been completed, the computer 11 controls the elevating driver 4 to return to the original vertical position for the measurements.

(43) Then, the rotary drive 5 is controlled to adjust the microscope head circumferentially to a next position, and measurements are made in circumferential sequence repeating the steps (32) to (41).

(44) With all measurements complete, the circumferential distribution of measured boundary widths is used to calculate a maximum grain boundary width.

(45) The average boundary width is calculated.

(46) According to the predetermined criteria, the degree of sensitization is determined.

Figure 20:
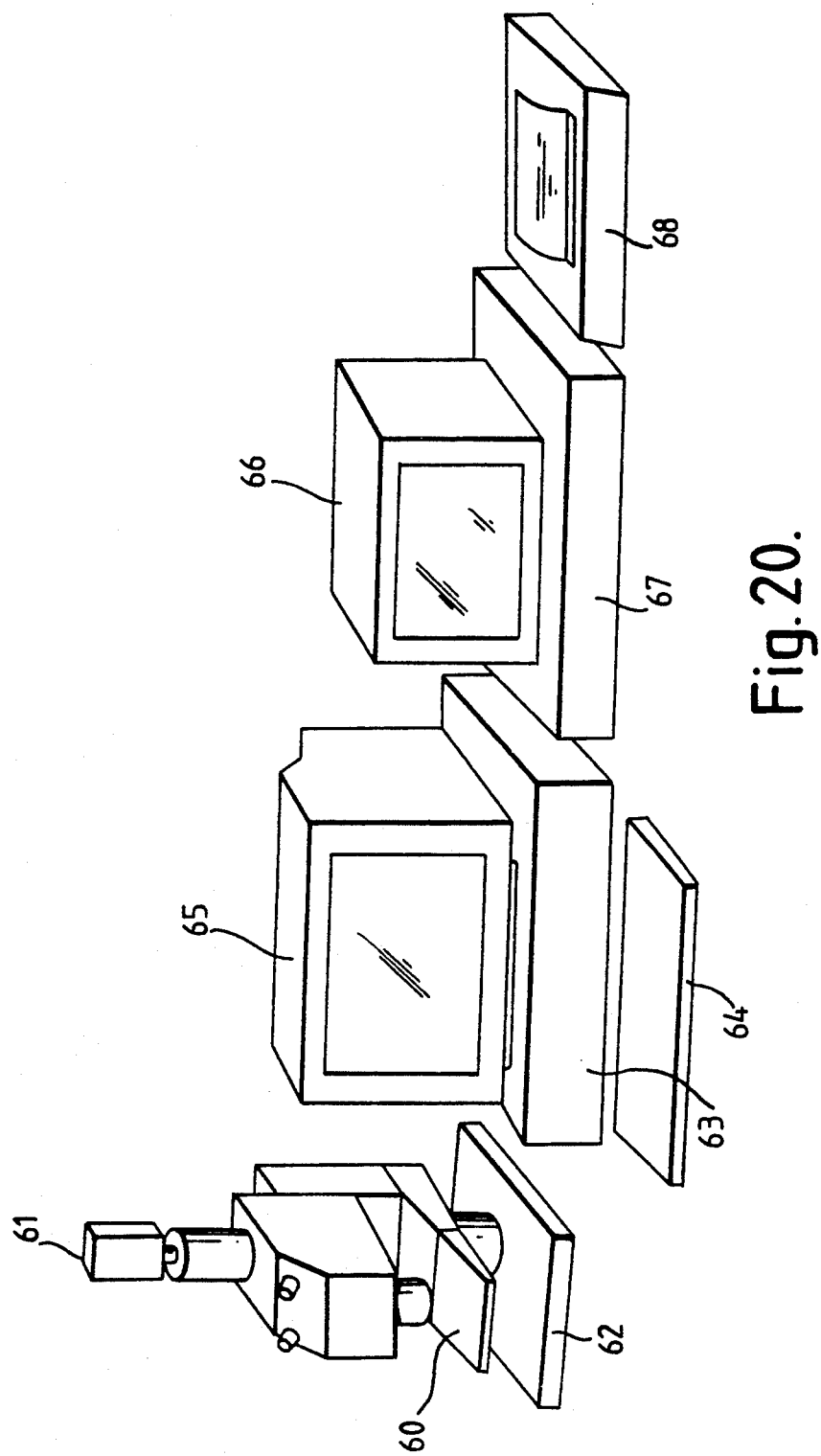

FIG. 20 shows apparatus for carrying out another embodiment. Especially dedicated apparatus such as that of FIG. 11 cannot always be used in certain practical situations. It is however sometimes possible to polish and etch a surface—perhaps manually—and prepare a replica thereof by using e.g. an acetylcellulose membrane. A magnified image of the replica is obtained e.g. through an ordinary optical microscope, and the image data fed to an image processor which can decide about sensitization on a basis as described above.

Specifically, a replica 60 is flattened e.g. by sandwiching between glass plates, or is placed on a glass plate and flattened down using tape. This is then placed on the sample holder of a microscope 62. An image formed by focusing the microscope 62 by eye is then input using a CCD camera 61 fitted onto the microscope and sent to an image processor 67 through a BNC cable. The microscope is then focused again, while studying the image displayed on the screen of a monitor 66, in order to specify a measurement area. A series of image processing operations can be performed interactively using a keyboard 64 e.g. according to a program menu displayed on the screen of CRT 65 by a computer 63. The result of the image processing is displayed on the screen of the CRT 65 and generated as a hard copy of the image, or as a list, by a printer 68.

It will be appreciated that the invention enables samples which need to be tested as to susceptibility e.g. welding heat-affected zones of a metal structure, to be examined by forming an image of the metal structure using a microscope, processing the image and measuring boundary widths therein. The testing can be used as a basis for selecting heat treatment, machining or other treatment to minimise the susceptibility of the zones concerned to SCC.

We claim:

1. A method for testing austenitic stainless steel to determine its susceptibility to stress corrosion cracking, comprising
   polishing and etching a surface of the steel;
   inputting an image of the polished and etched surface, through an optical microscope, into an image processor;
   identifying an etched grain boundary in the image;
   measuring the boundary width at said boundary in the image, using the image processor to determine the distribution of brightness across the grain boundary in the image, and
   comparing the measured boundary width with a predetermined reference width.

2. A method as claimed in claim 1, further comprising outputting a determined susceptibility status in dependence on the result of said comparison.

3. A method as claimed in claim 1, comprising making a plurality of said measurements of boundary width, calculating a mean width from said plural widths, and comparing the mean width with a reference mean width.

4. A method as claimed in claim 3 in which the reference mean width is fixed in the range from 1 to 1.5 $\mu$m.

5. A method according to claim 1, comprising measuring a plurality of boundary widths, determining a maximum width from said plurality of widths, and comparing the maximum width with a predetermined reference maximum width.

6. A method as claimed in claim 5 in which the reference maximum width is fixed in the range from 2 to 3 $\mu$m.

7. A method as claimed in claim 1 in which the step of measuring the boundary width comprises
   determining a maximum luminance of the image;
   setting a threshold luminance which is a predetermined proportion of said maximum luminance, and determining the extent of the boundary as the extent of the image, at the boundary, having less than said threshold luminance.

8. A method as claimed in claim 1 in which the step of measuring the boundary width comprises;
   determining a maximum luminance and minimum luminance of the image;
   setting a threshold luminance at a predetermined proportional level between the maximum luminance and minimum luminance, and
   determining the extend of the boundary as the extent of image, at the boundary, having less than said threshold luminance.

9. A method as claimed in claim 1, in which the etching step comprises electrolytic etching with oxalic acid.

10. A method as claimed in claim 1 in which the step of measuring boundary width comprises;
    determining whether a grain boundary identified in the image extends most nearly in one or the other of two perpendicular senses on the screen, and
    selecting a luminance distribution scan in that one of said two directions which is most nearly perpendicular to the grain boundary.

11. A method as claimed in claim 1 in which the step of measuring boundary width comprises;
    making a plurality of parallel luminance distributions cans across a portion of the grain boundary, to determine the extend thereof;
    from said scans, determining co-ordinates defining the orientation of the grain boundary direction relative to the scanning direction, and
    correcting the boundary extent determined by said scanning, according to said determined orientation, to derive the actual boundary width.

12. A method as claimed in claim 1, in which the process of identifying a grain boundary comprises selecting a measurement sub-area from the image, and carrying out luminance distribution measurement in said measurement sub-area.

13. A method as claimed in claim 12, comprising
    checking the luminance distribution within the measurement sub-area, and
    adjusting the measurement sub-area relative to the image, to improve the boundary width measurement obtainable therein.

14. A method for testing austenitic stainless steel to determine its susceptibility to stress corrosion cracking, comprising
    polishing and etching a surface of the steel;
    forming a replica of the polished and etched surface;
    inputting a magnified image of the replica into an image processor;
    determining at least one grain boundary location on the input image;
    measuring the boundary width on the image, across said at least one grain boundary, using the image processor;
    comparing the measuring boundary width with a predetermined reference width, and
    outputting a determined susceptibility status in dependence on said comparison.

15. A method for testing austenitic stainless steel, comprising;
    polishing and etching a surface of the steel;
    inputting a highly magnified image of the polished and etched surface, through a microscope, into an image processor;
    identifying at least one grain boundary in the image;
    making a plurality of width measurements across at least one grain boundary in the image;
    calculating a mean width from said plurality of width measurements;
    comparing the mean width with a stored reference mean width, fixed between 1 and 1.5 $\mu m$, and
    outputting a signal indicative of the susceptibility of the steel to stress corrosion cracking based on said comparison.

16. A method as claimed in claim 15, further comprising
    determining a maximum width from said plural measured widths, and
    comparing said maximum width with a predetermined reference maximum width.

17. Apparatus for testing austenitic stainless steel to assess the susceptibility thereof to stress corrosion cracking, the apparatus comprising;
    means for forming a magnified image of a polished and etched steel surface;
    an image processor;
    means for inputting said magnified image into said image processor;
    measuring means in the image processor, for measuring at least one boundary width in the image at a grain boundary therein, on the basis of a distribution of brightness in the image, and
    means for outputting a signal indicative of the susceptibility of the steel to stress corrosion cracking, in dependence on the at least one measured boundary width.

18. Apparatus as claimed in claim 17, comprising means for comparing the measured boundary width with a predetermined reference width.

19. Apparatus as claimed in claim 17, comprising display means for displaying an indication of said susceptibility.

20. Apparatus as claimed in claim 17, comprising means for measuring plural boundary widths from each image.

21. Apparatus as claimed in claim 20, comprising means for calculating a mean width from said plural measured boundary widths, and means for comparing the mean width with a reference mean width.

22. Apparatus as claimed in claim 20, comprising means for identifying a maximum width among said measured boundary widths, and means for comparing said maximum width with a predetermined maximum width.

23. Apparatus as claimed in claim 17, comprising means for specifying a sub-area of the image stored in the image processor as a measurement area for measurement of boundary widths, and means for varying the position of said sub-area in relation to the image.

24. Apparatus for use in determining the susceptibility of austenitic stainless steel to stress corrosion cracking, comprising
    an optical microscope;
    drive means for adjusting a position of said optical microscope in relation to a sample being tested;
    an image processor for receiving a magnified image from the optical microscope;
    means for selecting a measurement sub-area from the received image;
    means for making a plurality of boundary width measurements in said measurement sub-area, at at least one grain boundary location of the image;

means for calculating a mean width from said plurality of measured widths;

means for comparing the mean width with a predetermined reference mean width, and means for displaying a susceptibility status for the sample, in dependence on said comparison.

25. Apparatus as claimed in claim 24, comprising a camera for receiving the image from the optical microscope, and inputting the image to the image processor.

26. Apparatus as claimed in claim 24, comprising means for determining an orientation of a grain boundary direction relative to a width measurement scanning direction, and correcting a measured boundary width in dependence on said determined orientation.

* * * * *